(12) United States Patent
Shemesh et al.

(10) Patent No.: US 7,912,657 B2
(45) Date of Patent: Mar. 22, 2011

(54) METHOD AND SYSTEM FOR PROVIDING A COMPENSATED AUGER SPECTRUM

(75) Inventors: Dror Shemesh, Hod Hasharon (IL); Yuri Shirman, Rehovot (IL)

(73) Assignee: Applied Materials Israel, Ltd., Rehovot (IL)

( * ) Notice: Subject to any disclaimer, the term of this patent is extended or adjusted under 35 U.S.C. 154(b) by 205 days.

(21) Appl. No.: 11/877,125

(22) Filed: Oct. 23, 2007

(65) Prior Publication Data
US 2008/0234962 A1    Sep. 25, 2008

Related U.S. Application Data

(60) Provisional application No. 60/868,910, filed on Dec. 6, 2006.

(51) Int. Cl.
*G01B 5/28* (2006.01)
*G01K 1/08* (2006.01)
(52) U.S. Cl. .......................... 702/40; 250/399
(58) Field of Classification Search ............ 702/85, 702/104–107, 127, 156, 189, 57, 64–65, 702/75–76, 40; 250/201.3, 305, 311, 396 R, 250/397, 399, 493.1, 491.1; 378/4–5, 16, 378/19, 43, 70, 76; 850/1–4, 19, 21, 63
See application file for complete search history.

(56) References Cited

U.S. PATENT DOCUMENTS

| | | | | |
|---|---|---|---|---|
| 3,631,238 A | * | 12/1971 | MacDonald | 850/63 |
| 6,104,029 A | * | 8/2000 | Coxon et al. | 250/305 |
| 6,490,994 B1 | * | 12/2002 | Yoshizawa | 118/723 ER |
| 6,946,654 B2 | * | 9/2005 | Gerlach et al. | 850/3 |
| 7,456,399 B1 | * | 11/2008 | Soderstrom | 250/305 |

OTHER PUBLICATIONS

Patterson et al., A Non Contact Voltage Measurement Technique Using Auger Spectroscopy, 1983 IEEE/IRPS, pp. 150-152.*
Oswald et al., Factor Analysis and XPS-Data Preprocessing for Non-conducting Samples, 1999, Fresenius J Anal Chem 365, pp. 59-62.*

* cited by examiner

*Primary Examiner* — Michael P Nghiem
*Assistant Examiner* — Toan M Le
(74) *Attorney, Agent, or Firm* — SNR Denton US LLP (57) ABSTRACT

A system for providing a compensated Auger spectrum, the system includes: a processor, adapted to generate a compensated Auger spectrum in response to a non-compensated Auger spectrum and in response to an electric potential related parameter, and an interface to an electron detector that is adapted to detect electrons emitted from the first area, wherein the interface is connected to the processor, and wherein the electric potential related parameter reflects a state of a first area of an object that was illuminated by a charged particle beam during the generation of the non-compensated Auger spectrum.

19 Claims, 7 Drawing Sheets

METHOD AND SYSTEM FOR PROVIDING A COMPENSATED AUGER SPECTRUM

RELATED APPLICATIONS

This application is a Non-Provisional of, claims priority to and incorporates by reference U.S. Provisional Patent Application No. 60/868,910, filed 6 Dec. 2006.

FIELD OF THE INVENTION

The present invention relates to methods and systems for providing an Auger spectrum.

BACKGROUND

Measuring an Auger spectrum of a sample is a well known method for analyzing the composition of the sample. In particular this method is widely put to use in the semiconductors industry, in order to analyze contamination or composition of a surface of a sample. Auger Electron Spectrography (AES) analyzes the elements in a sample by directing an electron beam onto a selected area of the surface of the sample and scanning the kinetic energy of Auger electrons resulting from the impact of the electron beam.

During a standard AES process, the spectrometer counts detected Auger electrons emitted from the bombarded area in a wide range of energies (typically up to 2,500eV). In many cases, however, the actual potential of the analyzed area is not fully known, thus preventing an accurate determination of the actual energy of the Auger electron. Moreover, during a standard analysis performed by a conventional AES system, the bombardment of the sample by an electron beam, as well as several other factors known in the literature, can result in a charge accumulation effect of an insulating layer of the sample (if such a layer exists). The change of the electrical potential of the first area during the AES analysis leads to inaccuracies in the results of the analysis.

There is a need to provide an efficient method and system for providing a compensated Auger spectrum.

SUMMARY OF THE INVENTION

According to one embodiment of the invention, a system for providing a compensated Auger spectrum includes: a processor, adapted to generate a compensated Auger spectrum in response to a non-compensated Auger spectrum and in response to an electric potential related parameter; and an interface to an electron detector that is adapted to detect electrons emitted from a first area of an object that was illuminated by a charged particle beam during the generation of the non-compensated Auger spectrum, wherein the interface is connected to the processor, and wherein the electric potential related parameter reflects a state of the first area.

In a further embodiment of the invention a method for providing a compensated Auger spectrum includes: generating a compensated Auger spectrum in response to a non-compensated Auger spectrum and in response to an electric potential related parameter; wherein the electric potential related parameter reflects a state of a first area of an object that was illuminated by a charged particle beam during the generation of the non-compensated Auger spectrum.

BRIEF DESCRIPTION OF THE DRAWINGS

The present invention is illustrated by way of example, and not limitation, in the figures of the accompanying drawings, in which.

DETAILED DESCRIPTION

Figure 1:
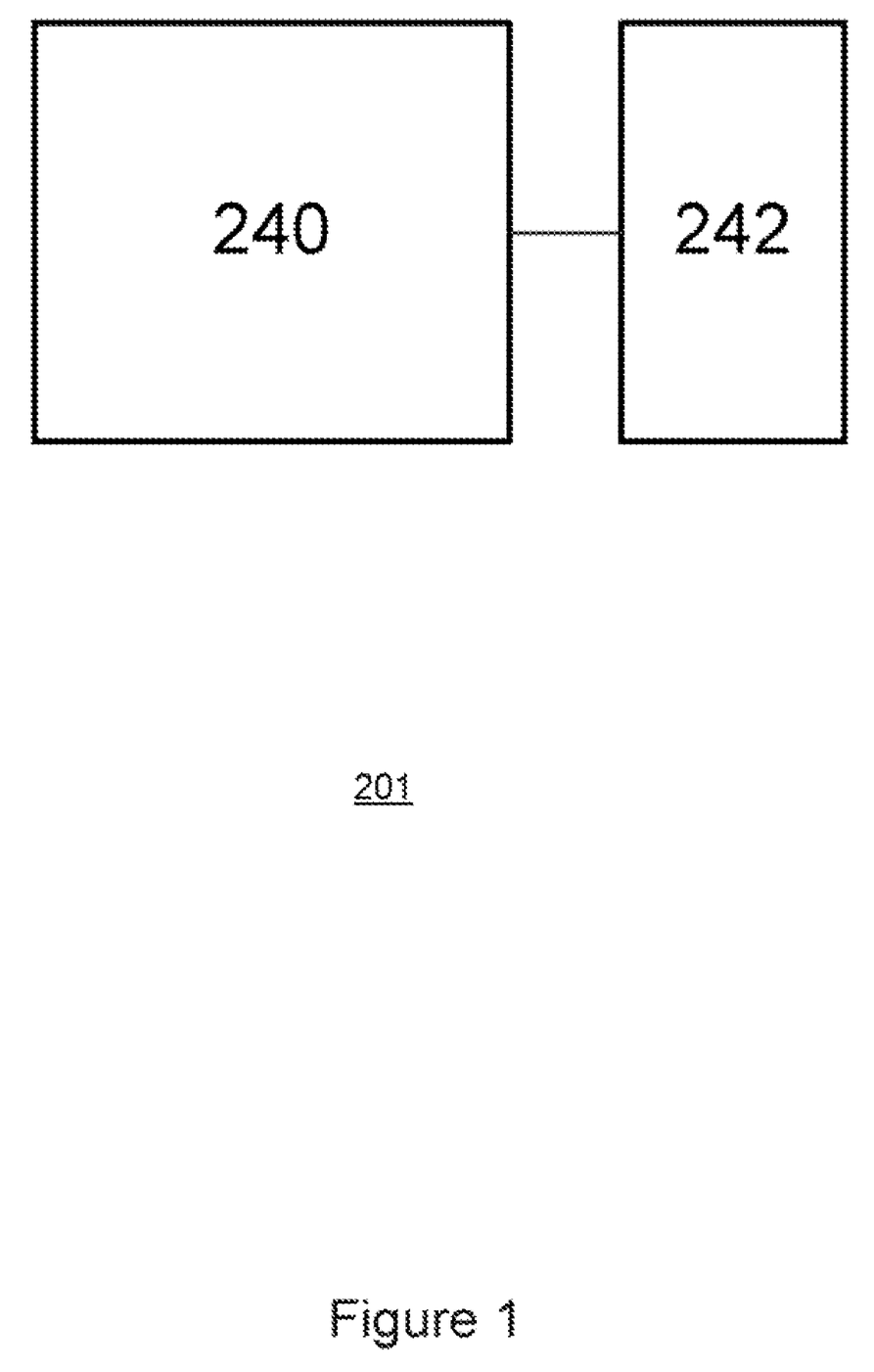
FIG. 1 illustrates a system for providing a compensated Auger spectrum, according to an embodiment of the invention.

FIG. 1 illustrates system 201 for providing a compensated Auger spectrum, according to an embodiment of the invention. System 201 includes processor 240, which is adapted to generate a compensated Auger spectrum in response to a non-compensated Auger spectrum and in response to an electric potential related parameter. Interface 242 that is connected to processor 240 is an interface to an electron detector, wherein the electron detector is adapted to detect electrons emitted from first area 101, whether detected by electron detector 220 of system 201 or an electron detector of an external system.

It is noted that the electric potential related parameter reflects a state of first area 101 of object 100 illuminated by a charged particle beam during the generation of the non-compensated Auger spectrum. The non-compensated Auger spectrum may be generated by system 201 or by an external system that provides it to system 201.

Figure 2:
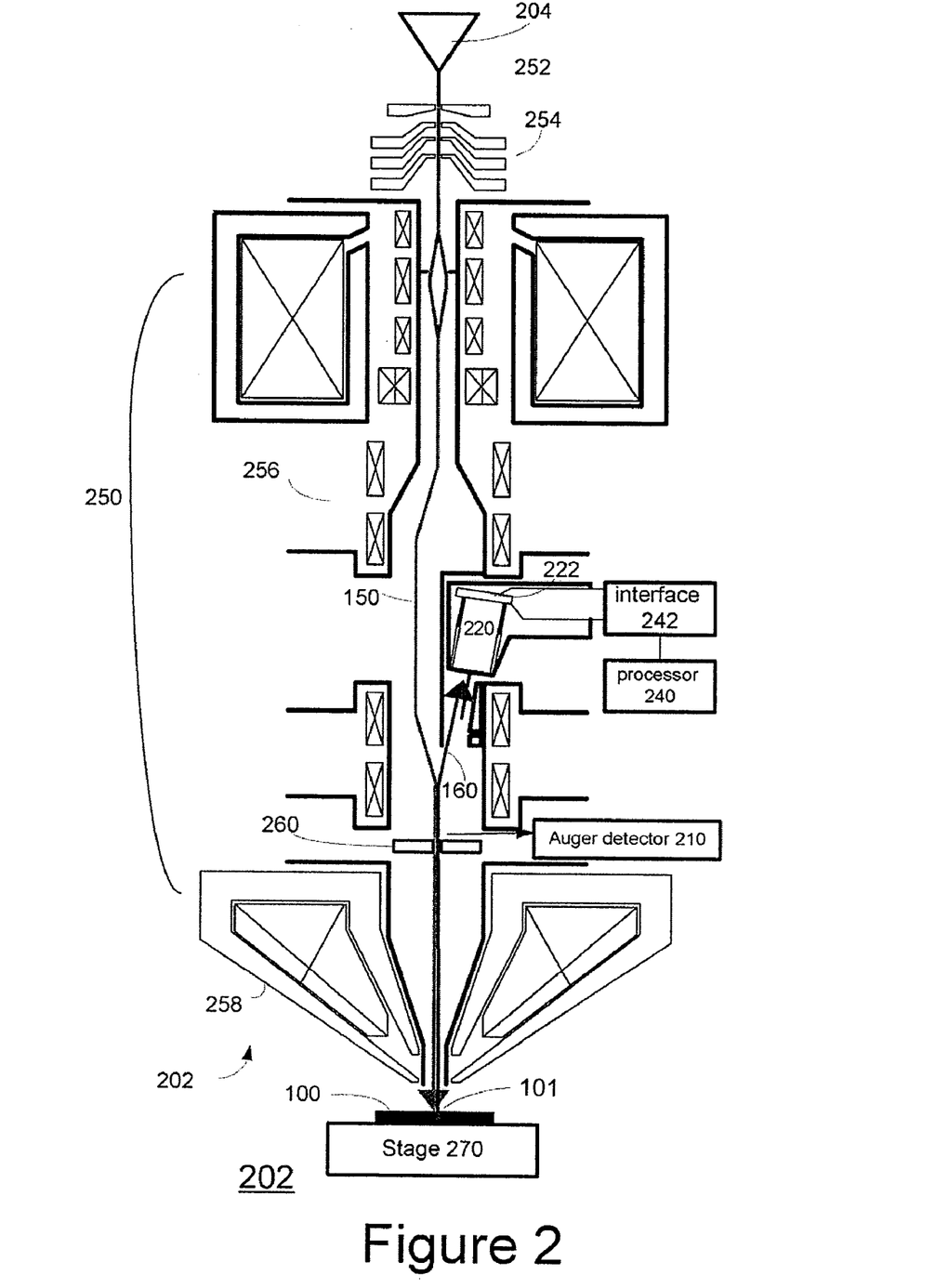
FIG. 2 illustrates a system for providing a compensated Auger spectrum, according to an embodiment of the invention.

FIG. 2 illustrates system 202 for providing a compensated Auger spectrum, according to an embodiment of the invention. System 202 is an Auger electron spectrography (AES) system that includes Auger detector 210 and also electron detector 220 which participates in the measuring of the electric potential related parameter.

System 202 includes: (i) Stage 270, for the supporting and positioning of object 100; (ii) electron gun 204 for generating a primary electron beam 150, (iii) multiple control and power supply units (not shown); (iv) optics 250 (that include, for example, elements 252, 254, 256, 258) which are adapted to illuminate a first area 101 with a primary electron beam 150 (conveniently, optics 250 are further adapted to direct a portion of the emitted electrons towards Auger detector 210 and another portion of the emitted electrons towards electron detector 220); (v) Auger detector 210, adapted to detect Auger electrons emitted from first area 101 and that are characterized by energy levels within a first energy band defined by processor 240; (vi) electron detector 220 which is adapted to detect secondary electrons emitted from first area 101, according to an energy based criterion defined by processor 240; and (vii) processor 240 which is connected to the Auger detector 210 and to electron detector 220 (directly or indirectly, wherein electron detector 220 is connected to processor 240 by interface 242). Processor 240 is adapted to: compute a material related parameter of first area 101 according to information received from electron detector 220, and to produce a compensated Auger spectrum of first area 101 in response to information received from Auger detector 210 and in response to the electric related parameter, which according to the this embodiment of the invention is the electric charge of first area 101.

According to an embodiment of the invention, optics 250 include condenser lens 252, a group of lenses 254 that includes aperture lens, aperture alignment and a stigmator. Group of lenses 254 is followed by additional deflectors collectively denoted 256 that cause primary electron beam 150 to deviate from the optical axis of system 202, while propagating in parallel to that axis. Deflectors 256 are followed by objective (as well as electrostatic) lens 258. Conveniently, system 202 may also include an additional in-lens detector 260, to gather additional information on first area 101 by analysis of secondary electrons emitted from first area 101.

Primary electron beam 150 is focused by objective lens 258 onto first area 101, and interacts with first area 101, which results in the reflection and the scattering of various types of electrons and photons, such as secondary electrons, backscattered electrons, Auger electrons and X-ray quanta. These reflected and scattered electrons (or at least a part of these electrons) form secondary electron beam 160 that moves upwards along the optical axis of system 202. Some Auger electrons of secondary electron beam 160 are then deflected towards Auger detector 210, while some other electrons of secondary electron beam 160 are deflected towards electron detector 220.

According to an embodiment of the invention, Auger detector 210 includes a first filter that is adapted to filter out electrons outside the first energy band; and wherein processor 240 is adapted to alter the first energy band. According to an embodiment of the invention, processor 240 is adapted to alter the first energy band in response to a measured electric potential related parameter. According to an embodiment of the invention, processor 240 is further adapted to compute a second energy band in response to the first energy band and to the electric potential related parameter.

According to an embodiment of the invention, electron detector 220 includes or is connected to an energy filter. Conveniently, electron detector 220 includes energy filter grid 222, which is adapted to filter out electrons with an energy level lower than a threshold value defined by processor 240.

It is noted that according to different embodiments of the invention, system 202 may include additional detectors, other than the detectors described above. According to some of the embodiments of the invention, system 202 includes at least one detector positioned in-lens and/or at least one external detector (not shown). System 202 may further include detectors of various types, such as a secondary electron detector, a backscattered electron detector, a narrowband X-ray detector, and the like, wherein each detector may include either a single sensing element, or an array of sensing elements. Furthermore, the additional detectors may be positioned to detect radiation emitted towards different directions.

It is further noted that, according to an embodiment of the invention, system 202, and especially optics 250, are further adapted to reduce an electrical charge of first area 101. According to an embodiment of the invention, optics 250 enables system 202 to scan a second area, which is significantly larger than first area 101. Those of skill in the art will appreciate that other well known charge reduction methods can be applied in different embodiments of the invention.

Figure 3:
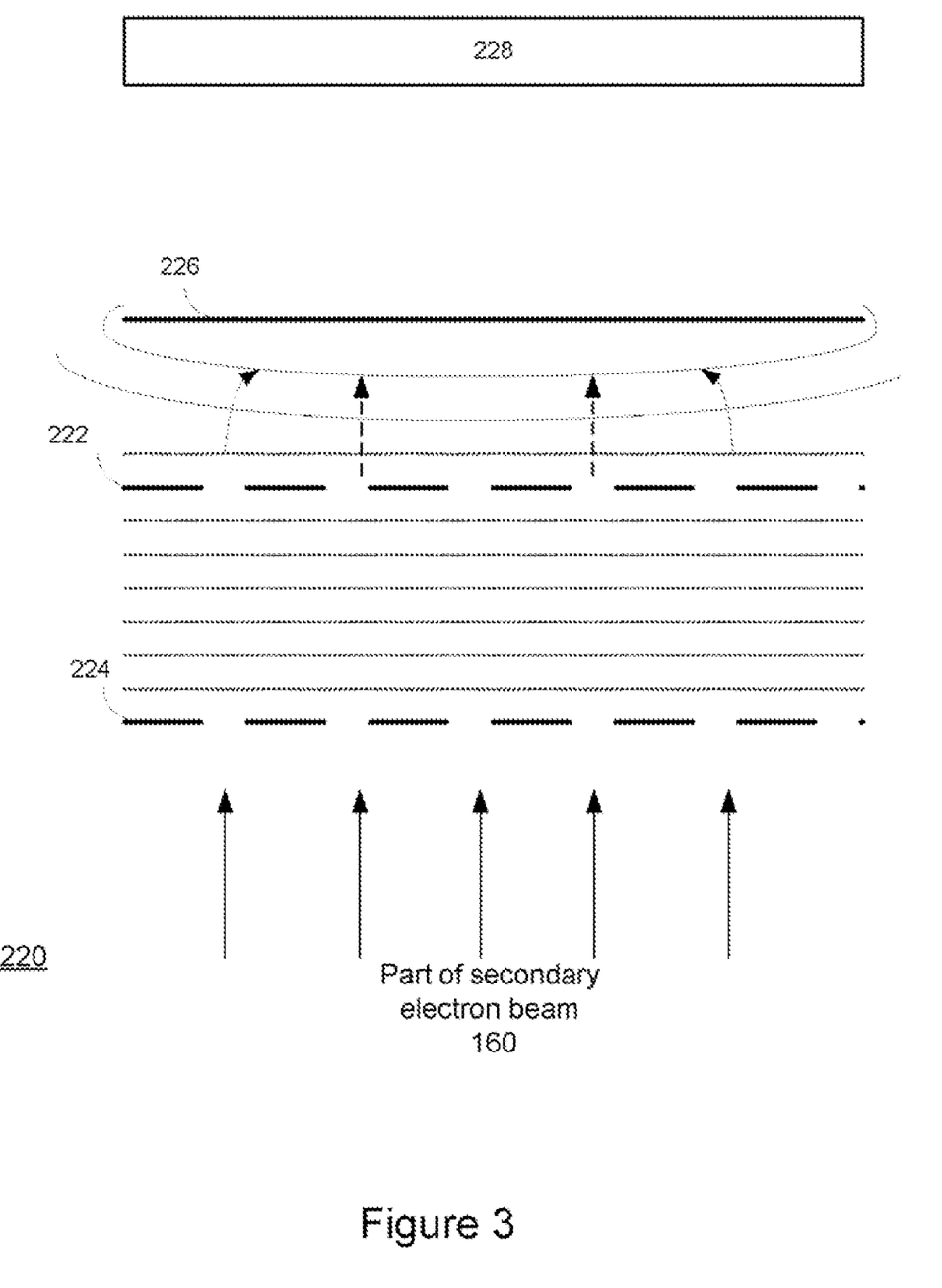
FIG. 3 is a detailed view of an electron detector configured according to an embodiment of the invention.

FIG. 3 is a detailed view of electron detector 220, according to an embodiment of the invention. Electron detector 220 includes energy filter grid 222 which is followed by detecting surface 226. Energy filter grid 222 may introduce electrostatic fields that may interfere with the primary electron beam 150. According to an embodiment of the invention, input grid 224, which is set to a potential difference that masks these electrostatic fields, is placed before energy filter grid 222. According to an embodiment of the invention, input grid 224 is set to the voltage of the column (about 8 Kv to 9 Kv), but it is noted that multiple other voltages can be applied. Equipotential lines are illustrated in FIG. 3 by fine dashed lines.

The vertical arrows as well as the curved arrows in FIG. 3 illustrate electrons from secondary electron beam 160 that arrive at electron detector 220. Some electrons propagate towards a detecting surface 226 while others are rejected. The electrons that reach the detecting surface 226 result in an emission of the electrons from detecting surface 226 that are converted to photons by scintillator 228. The light emitted from scintillator 228 is provided by a light guide (not shown) to a light sensor that provides signals which can be interpreted by processor 240.

The energy spectrum of secondary electrons that reach electron detector 220 or of an electron detector energy band which is responsive to an energy based criterion can be reconstructed by gradually changing a bias voltage supplied to energy filter grid 222. Processor 240 is adapted to control the bias voltage and to generate a set of intermediate results based upon a measurement of electrons filtered according to one or more of these bias voltages. Based upon those intermediate results, processor 240 is further capable of determining the electric potential related parameter of first area 101.

According to an embodiment of the invention, energy filter grid 222 is adapted to be configured in multiple different configurations and electron detector 220 is adapted to detect electrons filtered according to these multiple configurations concurrently with detection according to a single first energy band performed by the Auger detector.

Figure 4:
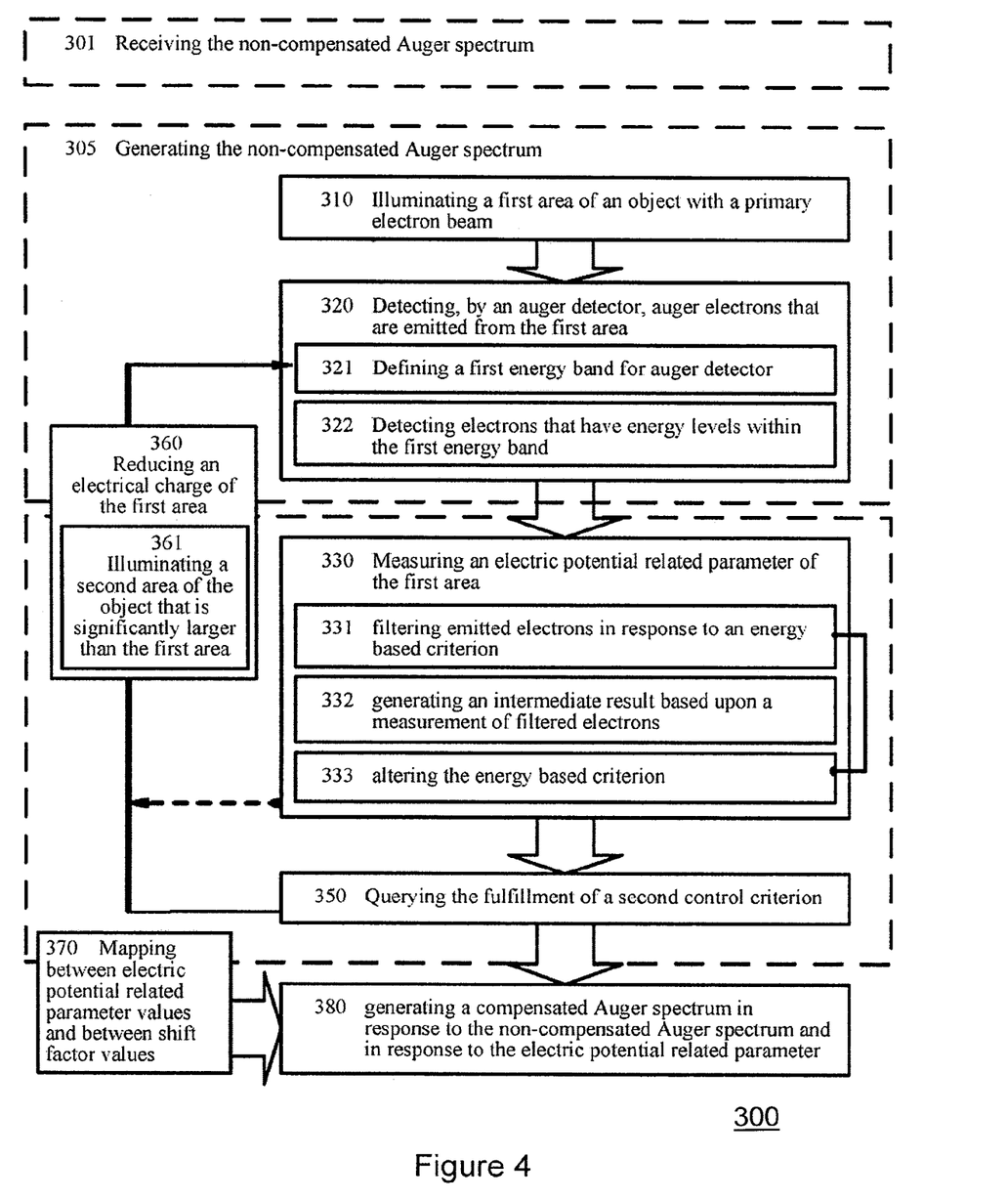
FIG. 4 illustrates a method for generating a compensated Auger spectrum according to an embodiment of the invention.

FIG. 4 illustrates method 300 for providing a compensated Auger spectrum of first area 101, according to an embodiment of the invention. Essentially method 300 includes generating a compensated Auger spectrum in response to a non-compensated Auger spectrum and in response to an electric potential related parameter; and wherein the electric potential related parameter reflects a state of a first area of an object that was illuminated by a charged particle beam during the generation of the non-compensated Auger spectrum.

Method 300 starts with either stage 301 of receiving the non-compensated Auger spectrum, or with stage 305 of generating the non-compensated Auger spectrum. Stage 305 starts with stage 310 of illuminating a first area of an object with a primary electron beam. Referring to the examples set forth in previous figures, system 202 illuminates first area 101 by a primary electron beam 150, using electron gun 204 and components of optics 250. It is noted that stage 310 may further include a scanning of the object for recognizing the first area, and a repositioning of the object in response to the scanning.

Stage 310 is followed by stage 320 of detecting, by an Auger detector, Auger electrons that are emitted from the first area. Referring to the examples set forth in previous figures, stage 320 is carried out by Auger detector 210.

According to an embodiment of the invention, stage 320 includes stage 321 of defining a first energy band for the Auger detector, which is followed by stage 322 of detecting electrons that have energy levels within the first energy band.

According to an embodiment of the invention, method 300 further includes stage 330 of measuring an electric potential related parameter of the first area. Conveniently, stage 330 measures the electric charge of the first area. It is noted that according to another embodiment of the invention, method 300 includes receiving the electric potential related parameter.

According to an embodiment of the invention, stage 330 includes stage 331 of filtering emitted electrons in response to an energy based criterion. In yet another embodiment of the invention, stage 331 is followed by stage 332 of generating an intermediate result based upon a measurement of filtered electrons. Stage 332 is followed by stage 333 of altering the energy based criterion. Conveniently, stage 330 may include multiple iterations of stage 331, 332 and 333, until a first control criterion is fulfilled. According to an embodiment of the invention, stage 330 includes (i) defining the electric potential related parameter in response to at least one intermediate result out of the set of intermediate results; and/or (ii) altering the energy based criterion in response to at least one intermediate result out of the set of intermediate results.

It is noted that stage 330 may be carried out at least partially concurrently to stage 320. It is further noted that stages 330, 331, 332 and 333 may all be repeated frequently enough in order to comply with the first control criterion in a pace that will enable the contemporaneous performing of stages 320 and 330.

According to an embodiment of the invention, stage 330 is followed by stage 350 of querying the fulfillment of a second control criterion, based upon the sufficiency of the information collected for a determination a material related parameter of the first area. The querying may relate to the electric potential related parameter; to information received from the detecting of Auger electrons; and to the material related parameter, or to any combination thereof. Method 300 then continues with the iteration of stages 320, 330 and 350, until the second control criterion is fulfilled.

According to an embodiment of the invention, method 300 further includes stage 360 of reducing an electrical charge of first area 101. It is noted that stage 360 may be carried out only during some of the iterations of stages 320, 330 and 350. According to an embodiment of the invention, stage 360 includes stage 361 of illuminating a second area of the object, which is significantly larger than the first area.

Method 300 continues with stage 380 of generating a compensated Auger spectrum in response to the non-compensated Auger spectrum and in response to the electric potential related parameter. It is noted that, according to an embodiment of the invention, stage 380 is preceded by stage 370 of mapping between electric potential related parameter values and between shift factor values of the Auger spectra.

Figure 5:
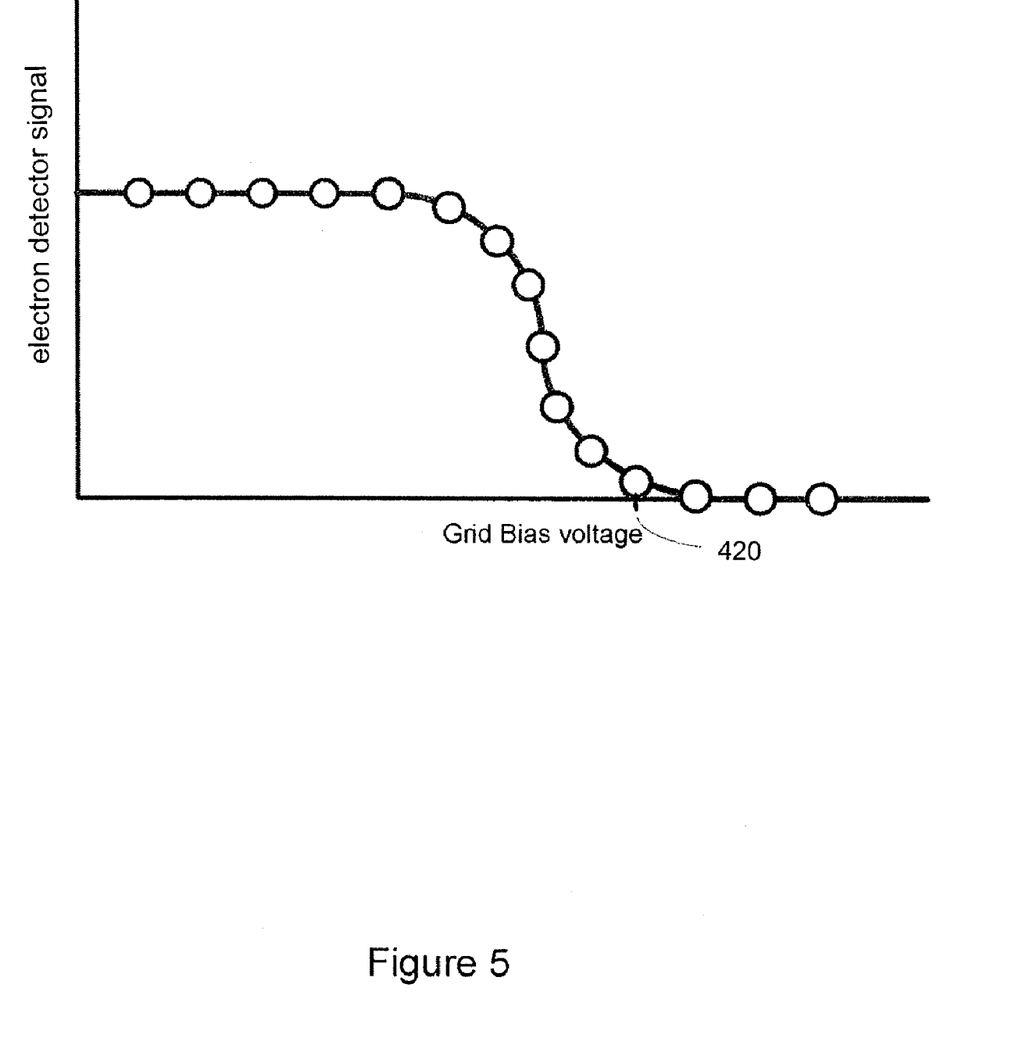
FIG. 5 illustrates multiple intermediate results according to an embodiment of the invention.

FIG. 5 illustrates multiple intermediate results according to an embodiment of the invention. The dots on the graph represent the intensity of the signal detected by electron detector 220, in various bias voltages applied to energy filter grid 222. When the bias voltage applied to energy filter grid 222 is low the signal is high, because no electrons are filtered out. When the bias voltage applied to energy filter grid 222 is high the signal nullifies, because all electrons are filtered out. Bias voltage 420 is the highest bias voltage applied to energy filter grid 222 that still enables a detection of positive signal by electron detector 220. According to such an embodiment of the invention, processor 240 is adapted to recognize bias voltage 420, and to determine the electric potential related parameter of first area 101 in response to bias voltage 420. For example, the value of bias voltage 420 (in Volts) may substantially equal the electric charge of first area 101.

Figure 6:
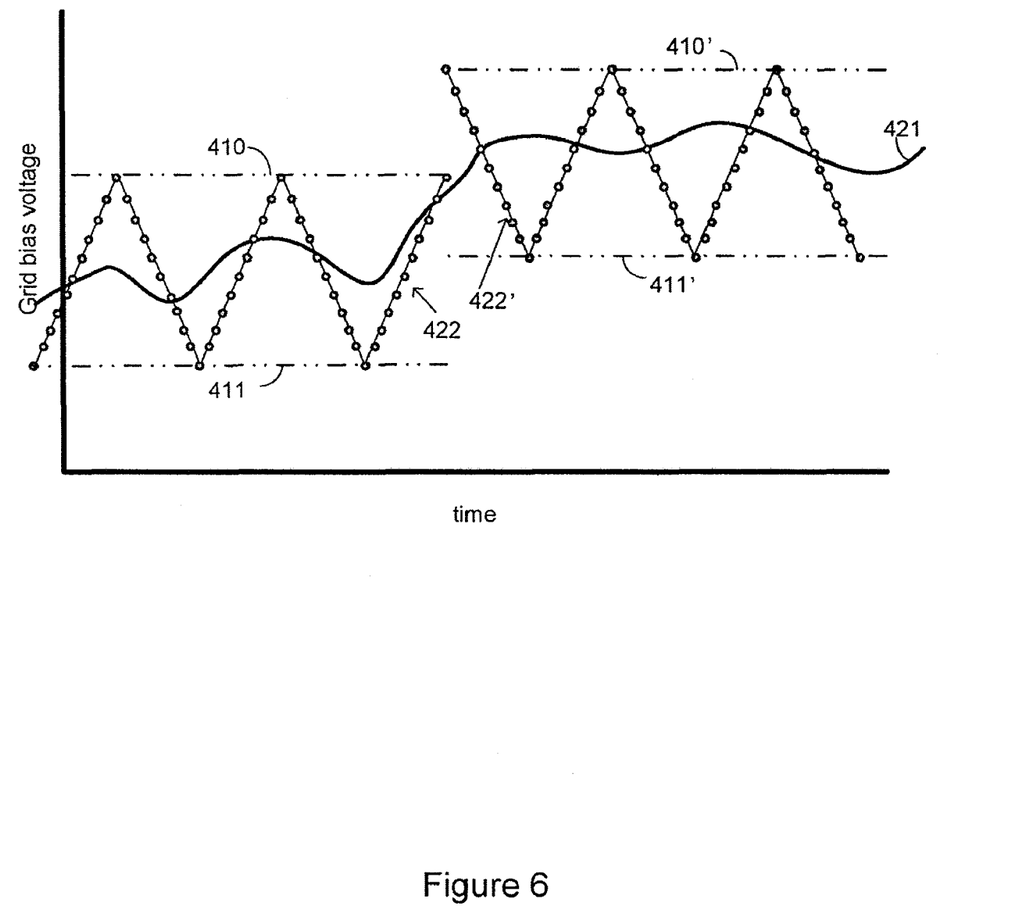
FIG. 6 illustrates an exemplary change of electrical potential and multiple intermediate results according to an embodiment of the invention.

FIG. 6 illustrates an exemplary change of electrical potential and multiple intermediate results according to an embodiment of the invention. Line 421 represents the electric charge of first area 101 over a period of time. Zigzagging lines 422 and 422' represent the bias voltage applied on the energy filter grid 222 at different times. The dots marked on lines 422 and 422' indicate measurements performed by electron detector 220 at different times.

According to such an embodiment of the invention, processor 240 is adapted to (i) define a high limit 410 and a low limit 411 to the bias voltage applied on the energy filter grid 222 according to the measured electric charge of first area 101; and to (ii) compare the electric charge of first area 101 to the limits 410 and 411.

Lines 410' and 411' in FIG. 6 illustrates the new limits 410 and 411, which are defined by the processor 240 in response to a comparison between the electric charge of first area 101 and to the previous limits 410 and 411, according to an embodiment of the invention.

Figures 7, 7A, 7B:
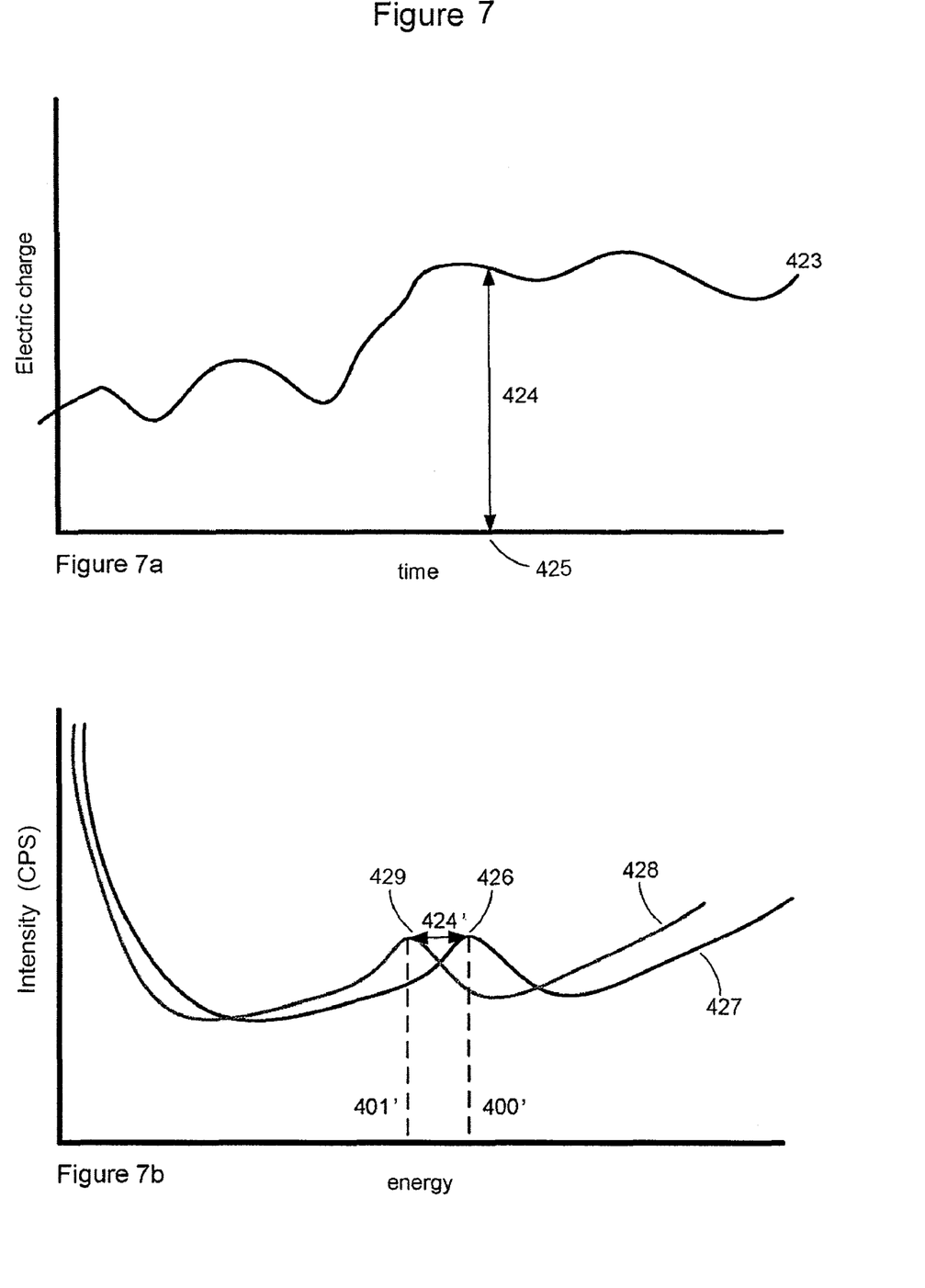
FIGS. 7a and 7b illustrate relationships between non-compensated Auger spectrums and compensated Auger spectrums according to embodiments of the invention.

FIG. 7 illustrates a relationship between a non-compensated Auger spectrum and a compensated Auger spectrum according to an embodiment of the invention.

Line 423 in FIG. 7a represents the electric charge of first area 101 in the midst of a measurement performed by system 202. At moment 425 in which energy peak 426 was measured by Auger detector 210 (illustrated in FIG. 7b), the electric charge of first area 101 was electric charge value 424.

FIG. 7b illustrates a non-compensated Auger spectrum 427 and a compensated Auger spectrum 428. Non-compensated Auger spectrum 427 is generated by matching the intensity of a signal detected by Auger detector 210 to an energy band that was applied at the time of the detection. Compensated Auger spectrum 428 is generated by matching the intensity of the signal detected by Auger detector 210 to a second energy band computed in response to the first energy band and to the electric charge of first area 101 at the time of the detection.

For example, at moment 425 in which energy peak 426 was measured, the energy band 400' was applied to Auger detector 210, and the processor computed a second energy band 401'. Energy peak 429 on compensated Auger spectrum 428 is the equivalent of energy peak 426 on non-compensated Auger spectrum 427. The energy difference 424' between the energies bands 400' and 401' corresponding to energy peaks 426 and 429 is determined by processor 240 in response to electric charge value 424 measured at moment 425.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method, comprising:
    measuring, using a measurement device, an electric potential related parameter of a first area of an object;
    generating, using a processor, a compensated Auger spectrum based upon a non-compensated Auger spectrum and based upon the electric potential related parameter, wherein (i) the electric potential related parameter reflects a state of the first area of the object illuminated by a charged particle beam during generation of the non-compensated Auger spectrum, (ii) the non-compensated Auger spectrum represents an Auger spectrum of the first area at first Auger electron-producing conditions, and (iii) the compensated Auger spectrum represents the Auger spectrum of the first area at second Auger electron producing conditions, wherein, generation of the non-compensated Auger spectrum comprises detecting Auger electrons emitted from the first area that have energy levels within a first energy band, altering the first energy band responsive to the measured electric potential parameter, and repeating detection of Auger electrons and alterating of the first energy band until a first control criterion is fulfilled.

2. The method according to claim 1, further comprising receiving the non-compensated Auger spectrum.

3. The method according to claim 1, further comprising generating the non-compensated Auger spectrum.

4. The method according to claim 1, wherein generation of the compensated Auger spectrum further comprises computing a second energy band in response to the first energy band and to the electric potential related parameter.

5. The method according to claim 1, wherein measuring the electric potential related parameter of the first area comprises filtering measured electrons based upon an energy based criterion; generating an intermediate result based upon a measurement of filtered electrons; altering the energy based criteria; repeating the filtering, the generating of the intermediate result and the altering to provide a set of intermediate results; and defining the electric potential related parameter in response to at least one intermediate result out of the set of intermediate results.

6. The method according to claim 5, further comprising detecting Auger electrons that are emitted from the first area and that have energy levels within a first energy band and wherein multiple iterations of the filtering, the generating of the intermediate result and the altering occur during a single iteration of detecting Auger electrons that have energy levels within the first energy band.

7. The method according to claim 1, further comprising reducing an accumulation of electrical charge of the first area.

8. The method according to claim 7, wherein reducing the accumulation of electrical charge comprises scanning a second area that is significantly larger than the first area.

9. A system for providing a compensated Auger spectrum of a first area of an object, comprising:

a processor adapted to generate the compensated Auger spectrum based upon a non-compensated Auger spectrum and based upon an electric potential related parameter, wherein the non-compensated Auger spectrum represents an Auger spectrum of the first area at first Auger electron-producing conditions, and the compensated Auger spectrum represents the Auger spectrum of the first area at second Auger electron-producing conditions; and an interface to an electron detector adapted to detect electrons emitted from the first area of the object illuminated by a charged particle beam during generation of the non-compensated Auger spectrum, wherein the interface is coupled to the processor, and wherein the electric potential related parameter reflects a state of the first area, wherein, generation of the non-compensated Auger spectrum comprises detecting Auger electrons emitted from the first area that have energy levels within a first energy band, altering the first energy band responsive to the measured electric potential parameter, and repeating detection of Auger electrons and alterating of the first energy band until a first control criterion is fulfilled.

10. The system according to claim 9, further adapted to receive the non-compensated Auger spectrum.

11. The system according to claim 9, further comprising optics adapted to illuminate the first area with a primary electron beam; and an Auger detector, coupled to the processor and adapted to detect electrons emitted from the first area, wherein the processor is further adapted to generated the non-compensated Auger spectrum in response to information provided by the Auger detector.

12. The system according to claim 11, wherein the Auger detector comprises a first filter adapted to filter out electrons outside a first energy band; and wherein the processor is further adapted to alter the first energy band.

13. The system according to claim 12, wherein the processor is further adapted to alter the first energy band in response to a measured electric potential related parameter.

14. The system according to claim 12, wherein the processor is further adapted to compute a second energy band in response to the first energy band and to the electric potential related parameter.

15. The system according to claim 11, wherein the optics are further adapted to reduce an accumulation of electrical charge of the first area.

16. The system according to claim 15, wherein the optics are further adapted to enable the system to scan a second area that is significantly larger than the first area.

17. The system according to claim 9, wherein the electron detector is further adapted to detect electrons emitted from the first area, and wherein the processor is further adapted to produce the electric potential related parameter of the first area in response to information provided by the electron detector.

18. The system according to claim 17, wherein the electron detector is coupled to a second filter that is adapted to selectively reject electrons based upon an energy based criterion, and the processor is further adapted to: (i) define and alter the energy based criterion, (ii) generate a set of intermediate results based upon a measurement of electrons filtered according to one or more energy based criteria; and (iii) define the electric potential related parameter in response to at least one intermediate result out of the set of intermediate results.

19. The system according to claim 18, wherein the second filter is adapted to be configured in multiple different configurations and the electron detector is further adapted to detect electrons filtered by these multiple configurations concurrently with the Auger detector detecting electrons according to a single first energy band.

* * * * *